(12) United States Patent
Merz et al.

(10) Patent No.: US 9,279,970 B2
(45) Date of Patent: Mar. 8, 2016

(54) OPTICAL IMAGING SYSTEM

(71) Applicant: Carl Zeiss Meditec AG, Jena (DE)

(72) Inventors: Franz Merz, Aalen (DE); Artur Hoegele, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 14/498,439

(22) Filed: Sep. 26, 2014

(65) Prior Publication Data
US 2015/0085357 A1 Mar. 26, 2015

(30) Foreign Application Priority Data

Sep. 26, 2013 (DE) .......................... 10 2013 219 379

(51) Int. Cl.
| | |
|---|---|
| G02B 21/00 | (2006.01) |
| A61B 3/12 | (2006.01) |
| G02B 21/02 | (2006.01) |
| G02B 21/22 | (2006.01) |

(52) U.S. Cl.
CPC .............. *G02B 21/0012* (2013.01); *A61B 3/12* (2013.01); *G02B 21/02* (2013.01); *G02B 21/22* (2013.01)

(58) Field of Classification Search
CPC .... G02B 21/0012; G02B 21/02; G02B 21/22; A61B 3/12
USPC .......................... 359/376, 379, 381, 656–661
See application file for complete search history.

(56) References Cited

U.S. PATENT DOCUMENTS

| | | | |
|---|---|---|---|
| 3,883,231 A * | 5/1975 | Koizumi ........................ 359/660 |
| 4,518,231 A | 5/1985 | Muchel et al. | |
| 6,598,972 B2 | 7/2003 | Strahle | |
| 6,788,455 B2 | 9/2004 | Kirchhuebel et al. | |
| 6,943,942 B2 | 9/2005 | Horiguchi et al. | |
| 6,967,774 B2 | 11/2005 | Kirchhuebel et al. | |
| 7,085,046 B2 | 8/2006 | Horiguchi et al. | |
| 7,408,705 B2 | 8/2008 | Horiguchi et al. | |
| 7,570,408 B2 * | 8/2009 | Higuchi ..................... 359/221.1 |
| 7,791,794 B2 | 9/2010 | Reimer et al. | |
| 7,839,494 B2 | 11/2010 | Reimer et al. | |
| 8,023,120 B2 | 9/2011 | Reimer et al. | |
| 2005/0012992 A1 * | 1/2005 | Kitajima ....................... 359/381 |
| 2005/0190436 A1 * | 9/2005 | Terada et al. ................. 359/381 |

FOREIGN PATENT DOCUMENTS

| | | |
|---|---|---|
| DE | 35 39 009 A1 | 5/1987 |
| DE | G 94 15 219.5 U1 | 11/1994 |
| DE | 10 2010 018 123 A1 | 10/2011 |

* cited by examiner

*Primary Examiner* — Frank Font
(74) *Attorney, Agent, or Firm* — Walter Ottesen P.A.

(57) ABSTRACT

An optical imaging system generates an image of an object plane and includes a lens system which, in turn, includes a main objective and a reduction optical unit ahead of the main objective. The lens system is aligned along an optical axis and the reduction optical unit includes a first lens with a positive refractive power and a second lens with a negative refractive power. An object-side first main plane and an image-side second main plane are defined by the lens system. The optical imaging system defines an observation beam path which is guided through the lens system so that, in the first main plane and in the second main plane, the observation beam path is at a distance (B) from the optical axis. The first lens is of a first material having a first Abbe number and the second lens is of a second material having a second Abbe number, wherein the first Abbe number is greater than the second Abbe number.

8 Claims, 3 Drawing Sheets

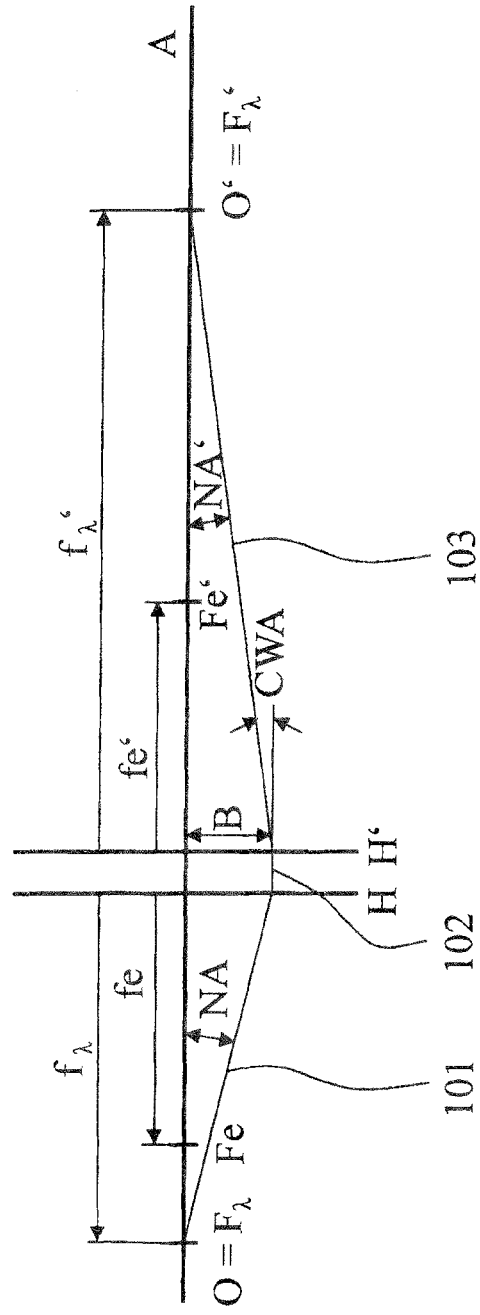

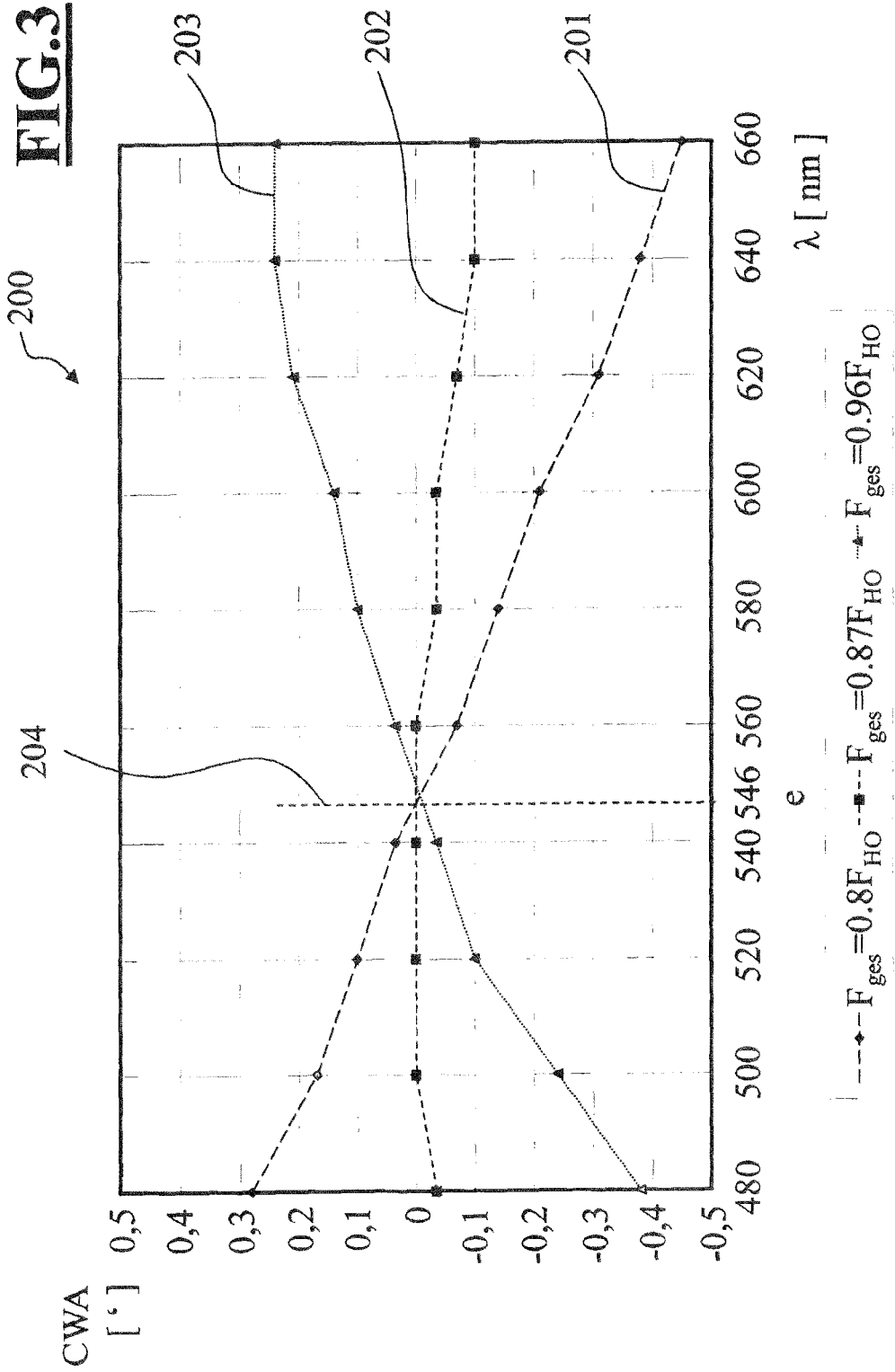

OPTICAL IMAGING SYSTEM

CROSS REFERENCE TO RELATED APPLICATION

This application claims priority of German patent application no. 10 2013 219 379.3, filed Sep. 26, 2013, the entire content of which is incorporated herein by reference.

FIELD OF THE INVENTION

The invention relates to an optical imaging system, in particular a microscope, for generating an image of an object plane, including a lens system which includes a main objective and a reduction optical unit between the main objective and the object plane and which is aligned along an optical axis. The reduction optical unit includes a first lens with a positive refractive power and a second lens with a negative refractive power. An object-side first main plane and an image-side second main plane are defined by the lens system. The optical imaging system defines an observation beam path which is guided through the lens system in such a way that, in the first main plane and in the second main plane, the observation beam path in each case has a distance from the optical axis of the lens system.

When observing an object through an optical imaging system, in particular through a stereo surgical microscope, a wide angle optical unit can be introduced into the beam path between the main objective of the optical imaging system and the object to be observed, for example an eye. This enables observation of the fundus. In addition to this wide angle optical unit, a reduction optical unit can be pivoted into the beam path between the wide angle optical unit and the main objective of the optical imaging system in order to enable the adaptation of the wide angle optical unit to an optical imaging system, for example a surgical microscope.

BACKGROUND OF THE INVENTION

U.S. Pat. Nos. 6,788,455 and 6,967,774 have disclosed a microscope for wide angle observation for ophthalmic surgery which, by way of selectively addable optical units, allows an image of the fundus to be generated. The microscope includes a lens system, which includes a main objective and lenses disposed ahead of the main objective.

A disadvantage of this microscope is that the imaging quality in the wide angle observation is not ideal. As a result of the small distance between the main objective and the object to be observed, very short focal lengths result for a wide angle optical unit that can be added to the beam path. The wide angle optical unit can be adapted to the microscope by means of a further reduction optical unit which can be introduced into the beam path; however, this is linked to the disadvantage of a reduced imaging quality.

In addition to the optical disadvantages, the optical imaging systems in accordance with U.S. Pat. Nos. 6,788,455 and 6,967,774 have a relatively long installation length. In order not to unnecessarily hinder the user, for example a surgeon, in his work with the optical imaging system on the object, for example a patient eye, a reduction optical unit should only have a short installation length and additionally be disposed as closely as possible to the main objective.

SUMMARY OF THE INVENTION

It is an object of the invention to provide an optical imaging system, in which a very high imaging quality is achieved when using a reduction optical unit ahead of a main objective. Furthermore, it is an object to provide an imaging system with a short structural length.

According to the invention, this object is achieved by virtue of the first lens of the reduction optical unit being manufactured from a first material which has a first Abbe number, and of the second lens of the reduction optical unit being manufactured from a second material which has a second Abbe number, wherein the first Abbe number is greater than the second Abbe number. Here, the lens system is configured in such a way that the following relation is satisfied for a wavelength range $\lambda$ of 480 nm$\leq\lambda\leq$660 nm and for a main wavelength e=546 nm:

$$\left|\arctan\left(\frac{B}{f'_e + (f_e \cdot f'_e / (f_\lambda - f_e))}\right)\right| < 0.5',$$

where:
B=distance between an observation beam path and the optical axis in the first main plane H;
$f_e$=object-side focal length for the main wavelength e in respect of the first main plane H;
$f_\lambda$=object-side focal length for the wavelength $\lambda$ in respect of the first main plane H;
$f'_e$=image-side focal length for the main wavelength e in respect of the second main plane H'.
The term "0.5'" has units of minutes of arc.

If the lens system is embodied in such a way that the following condition is satisfied for all wavelengths $\lambda$ between 480 nm and 660 nm and for a main wavelength e=546 nm $$\left|\arctan\left(\frac{B}{f'_e + (f_e \cdot f'_e / (f_\lambda - f_e))}\right)\right| < 0.5',$$

then the imaging quality for an observation beam path is so good that contrast-reducing and bothersome aberrations are corrected, and so an unchanging high contrast of the imaging and an unchanging high image quality are achieved over the whole wavelength range $\lambda$.

In one embodiment of the invention, the first material and the second material are selected in such a way that a difference between the first Abbe number and the second Abbe number lies between 16 and 22.

When designing the lens system, it was found to be particularly advantageous to select the first material of the lens with the positive refractive power and the second material of the lens with the negative refractive power in such a way that the difference in the Abbe numbers of the two materials lies between 16 and 22. Using this, the described condition can be satisfied well and a very good contrast advantageously emerges over the whole wavelength range while having a low chromatic angle deviation. Particularly advantageously, the lens with the positive refractive power is formed from a material with a high Abbe number and the lens with the negative refractive power is formed from a material with a low Abbe number, wherein the difference in the Abbe numbers lies between 16 and 22.

In a further embodiment of the invention, the first material and the second material are selected in such a way that a first refractive index of the first material is greater than 1.6 and a second refractive index of the second material is greater than 1.6.

The aforementioned condition can be satisfied well by using materials with high refractive indices, that is greater than 1.6, for the first and second lenses of the reduction optical unit. As a result, a well corrected image with a very good contrast and a low chromatic angle deviation advantageously emerges.

In a further embodiment of the invention, the first lens is disposed in a stationary manner and the second lens is disposed displaceably in the direction of the optical axis.

The distance of the object plane to be observed from the main objective may vary. As a result, it may be necessary to adapt the focus of the optical observation apparatus to the modified object plane. In order to allow the focus setting of the microscope to stay unchanged, it is advantageous if the reduction optical unit offers the option of focusing. This focusing option can be achieved relatively easily by virtue of the first lens of the reduction optical unit being disposed in a stationary manner and the second lens being able to perform a relative movement along the optical axis. With the optical imaging system of the invention, a good correction of the chromatic angle deviation is ensured over the whole focusing range.

In a further embodiment of the invention, the second lens is disposed in a stationary manner and the first lens is disposed displaceably in the direction of the optical axis.

The same advantages as described in the preceding embodiment can be achieved if the second lens of the reduction optical unit is disposed in a stationary manner and the first lens of the reduction optical unit is disposed displaceably in the direction of the optical axis.

In a further embodiment of the invention, the reduction optical unit can be pivoted into the beam path ahead of the main objective.

In order to enable the user of a microscope to work alternatively with or without the reduction optical unit, it is advantageous if the reduction optical unit can be simply introduced into the beam path or removed from the beam path. As a result, the user can quickly and easily switch back-and-forth between two focus planes without having to change the focus setting of the microscope. Advantageously, the reduction optical unit can be pivoted into and out of the beam path ahead of the main objective very easily and quickly by means of a pivoting device.

In a further embodiment of the invention, a further optical element for generating an intermediate image is mounted in the observation beam path ahead of the reduction optical unit and the optical imaging system is focused onto the intermediate image.

A further optical element can be introduced into the beam path ahead of the reduction optical unit. The observed object plane can then constitute an intermediate image plane, which emerges spatially in the beam path between the further optical element and the reduction optical unit. Deficiencies in the imaging quality resulting from the introduction of the further optical element can particularly advantageously be corrected chromatically by the reduction optical unit such that a very good high-contrast image without image offset can be observed.

In a further embodiment of the invention, the optical imaging system is embodied as a stereo microscope which includes a first observation beam path and a second observation beam path, wherein, in the first main plane H and in the second main plane H', the first and the second observation beam paths each have a distance B from the optical axis of the lens system.

The lenses of the reduction optical unit are usually embodied in a rotationally symmetric manner with respect to the optical axis. As a result of the optical axis of the main objective and the optical axis of the reduction optical unit being identical, the optical chromatic correction for all observation beam paths extending at a distance B from the optical axis with respect to the two main planes H and H' is equally good. For a stereo microscope, an advantage emerging from this is that both observation beam paths are corrected equally well chromatically by a single reduction optical unit. This advantage also applies to each further observation beam path guided at a distance B from the optical axis in respect of the two main planes H and H'.

BRIEF DESCRIPTION OF THE DRAWINGS

The invention will now be described with reference to the drawings wherein:

FIG. 2 shows a schematic of a beam path in an optical imaging system in accordance with FIG. 1; and, FIG. 3 shows an image-side chromatic angle deviation in relation to a wavelength of between 480 nm and 660 nm for three different focal lengths of the optical imaging system in accordance with FIG. 1.

Figure 1:
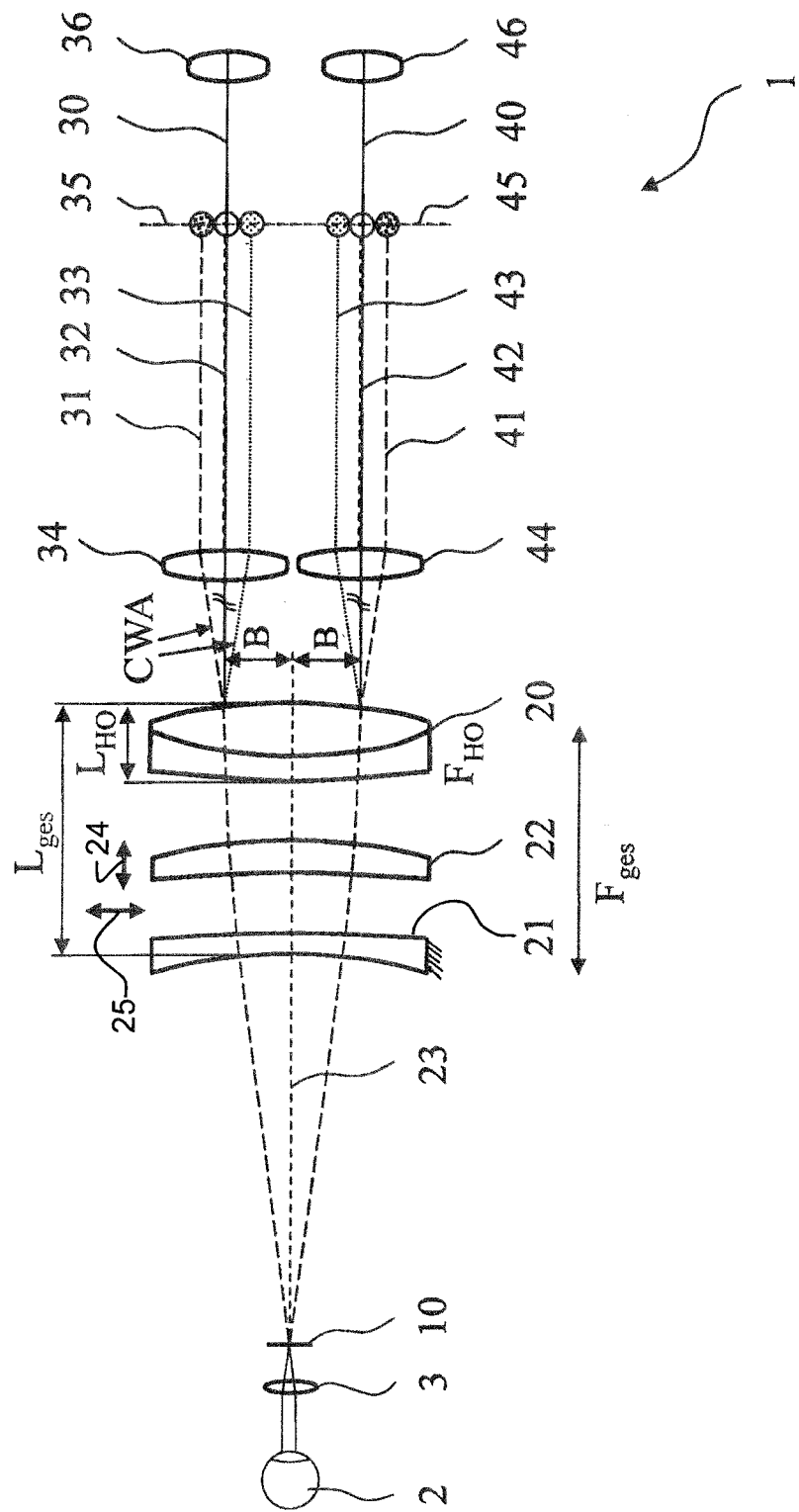
FIG. 1 shows a first embodiment of an optical imaging system according to the invention, including a reduction optical unit mounted ahead of a main objective.

DESCRIPTION OF THE PREFERRED
EMBODIMENTS OF THE INVENTION

FIG. 1 depicts an exemplary embodiment of an optical imaging system 1 according to the invention, including a reduction optical unit mounted ahead of a main objective 20.

The exemplary embodiment shows an optical imaging system 1 for observing an eye 2. The optical imaging system 1 is configured as a stereoscopic observation system with a right-hand observation beam path 30 and a left-hand observation beam path 40 and includes a main objective 20 with an optical axis 23, a right-hand tube lens 34, a left-hand tube lens 44 and a right-hand eyepiece 36 and a left-hand eyepiece 46. It may comprise further optical elements not depicted here.

A further optical element in the form of an ophthalmic lens 3 and a reduction optical unit in the form of two lenses have been introduced into the beam path between the main objective 20 and the eye 2. A first lens of the reduction optical unit disposed directly ahead of the main objective 20 is embodied as a positive lens 22 and has a positive refractive power. A second lens of the reduction optical unit is embodied as a lens with negative refractive power, as a negative lens 21.

The right-hand observation beam path 30 and the left-hand observation beam path 40 pass through the ophthalmic lens 3 and may cross in an image plane 10. The right-hand observation beam path 30 emanating from the image plane 10 passes through the negative lens 21, the positive lens 22, the main objective 20, the right-hand tube lens 34 and reaches the right-hand eyepiece 36. Here, an eyepiece intermediate image, which can be observed through the right-hand eyepiece 36 by an observer, is generated in a right-hand eyepiece intermediate image plane 35 in the right-hand observation beam path 30. The left-hand observation beam path 40 emanating from the image plane 10 is guided through the negative lens 21, the positive lens 22, the main objective 20, the left-hand tube lens 44 to the left-hand eyepiece 46. Here, an eyepiece intermediate image, which can be observed through the left-hand eyepiece 46 by an observer, is generated in a left-hand eyepiece intermediate image plane 45 in the left-hand observation beam path.

Downstream of the main objective 20, the right-hand observation beam path 30 extends parallel to the optical axis 23. This parallel distance is denoted by B. Accordingly, the left-hand observation beam path 40 likewise extends parallel to the optical axis 23 at a distance B downstream of the main objective 20. The parallel distance between the two observation beam paths (30, 40) downstream of the main objective 20 may also be referred to as a stereo base SB, wherein the stereo base SB has a value double that of the distance B. A typical numerical value for the stereo base SB may be 25 mm.

Typical values for the focal lengths of the ophthalmic lens 3 are 60 diopter, 90 diopter or 120 diopter. The short focal length of the ophthalmic lens 3 may be a cause for occurring aberrations, which are referred to as spectral tilting of the optical axes or as a chromatic angle deviation CWA.

FIG. 1 schematically shows the effects of the chromatic angle deviation CWA. The chromatic angle deviation CWA should be understood to mean a color-dependent chromatic image offset between the eyepiece intermediate images, perpendicular to the optical axis 23.

Due to a symmetric design, the same values in terms of magnitude are to be expected for the chromatic angle deviation CWA of the right-hand observation beam path 30 and of the left-hand observation beam path 40. A chromatic angle deviation may also occur for a single observation beam path. Chromatic angle deviations for three wavelength ranges in the form of three sub-beams are depicted for the right-hand observation beam path 30: a right-hand red component beam 31, a right-hand green component beam 32 and a right-hand blue component beam 33. A chromatic angle deviation for three wave regions in the form of a left-hand red component beam 41, a left-hand green component beam 42 and a left-hand blue component beam 43 is depicted for the left-hand observation beam path 40. The image offset of the right-hand component beams (31, 32, 33) in the right-hand observation beam path 30 in the right-hand eyepiece intermediate image plane 35 is visible through the right-hand eyepiece 36. The image offset of the left-hand component beams (41, 42, 43) in the left-hand observation beam path 40 in the left-hand eyepiece intermediate image plane 45 is visible through the left-hand eyepiece 46.

Without chromatic correction, the image offset caused by the chromatic angle deviation CWA is perceived to be contrast-reducing and bothersome. If this chromatic image offset is above the resolution limit of the eye, the observer perceives colored double images. The green wavelength range, in the form of the green component beams (32, 42), is depicted in the center of the eyepieces. The blue image region in the form of the blue component beams (33, 43) is visible within the region between the two eyepiece centers. The red wavelength range, in the form of the red component beams (31, 41), is visible outside of the region between the eyepiece centers.

In this exemplary embodiment, the reduction optical unit, which includes the positive lens 22 and the negative lens 21, is disposed very closely to the main objective 20. The main objective 20 has a structural length $L_{HO}$. The thickness or extent of the main objective 20 along the optical axis 23 is referred to as structural length $L_{HO}$. An overall structural length $L_{ges}$ refers to the greatest extent of the main objective 20 and the reduction optical unit, which includes the negative lens 21 and the positive lens 22, in relation to the optical axis 23. By way of example, if the main objective 20 has a structural length $L_{HO}=1$ cm, $L_{ges}<3.2$ cm emerges for the overall structural length.

As a result of the very close arrangement of the reduction optical unit ahead of the main objective 20, the provision of a high-contrast, chromatically corrected image region with a very high imaging quality constitutes a particular challenge.

Reference should still be made to the fact that the image plane 10 depicted in this exemplary embodiment is represented as an intermediate image plane, in which the right-hand observation beam path 30 and the left-hand observation beam path cross. The image plane 10 may also constitute a different object plane to be observed. Likewise, the position of the negative lens 21 and the position of the positive lens 22 may be disposed in an interchanged manner.

FIG. 2 shows a schematic of a beam path of the optical imaging system 1 in accordance with FIG. 1.

An optical axis A is drawn as thick horizontal line. Perpendicular to the optical axis A, a first main plane H serves as reference plane for focal lengths or distance data in the object space and a second main plane H' serves as reference plane for the image space. The two main planes (H, H') render it possible to describe the effect of the complex optical lens system by the equation valid for a thin lens. The first main plane H and the second main plane H' are both defined perpendicular to the optical axis of the lens system and therefore extend parallel to one another. The two main planes (H, H') replace the main objective 20 and the reduction optical unit, which includes the negative lens 21 and the positive lens 22.

The optical lens system images an object point O on an image point O'. From the object point O, a first ray 101 extends to the first main plane H at an angle NA in relation to the optical axis A. The angle NA is also referred to as object-side numerical aperture. A second ray 102 extends parallel to the optical axis A between the first main plane H and the second main plane H'. In each of the first main plane H and the second main plane H', the second ray 102 is at a distance B from the optical axis A. In the case of a stereoscopic imaging system, B may have a value which, in terms of magnitude, corresponds to the numerical value of half of the stereo base SB. When emerging from the second main plane H', a third ray 103 is directed to the image point 0'. The third ray 103 includes an angle CWA with the optical axis A. The angle CWA represents the image-side chromatic angle deviation CWA. If the image-side chromatic angle deviation CWA equals zero, the image point O' lies at infinity.

For the object space, an object-side focus Fe has the object-side focal length fe for a main wavelength e. In the image space, the image-side focus Fe' has the image-side focal length fe' for the main wavelength e. Therefore, an object-side focal length $f\lambda$ for an object-side focus $O=F\lambda$ and an image-side focal length $f\lambda'$ for an image-side focus $O'=F\lambda'$ emerge conformally for a wavelength λ.

In order to solve the problem, it was found that the chromatic angle deviation CWA measure constitutes a very good option for evaluating measures for optimizing the image quality. Expediently, a main wavelength e=546 nm is assumed when calculating the optical unit. The main wavelength e is also referred to as Fraunhofer line e and defines the main wavelength in the green spectral range of the sun. In order to image an object point O, for example the image plane 10, with high contrast and a very good imaging quality, it is necessary to provide an optical unit which is chromatically corrected over the visible wavelength range λ between 480 nm and 660 mm.

The reduction optical unit which includes the negative lens 21 and the positive lens 22 which are manufactured from different materials, is disposed ahead of the main objective 20. In order to achieve a good image quality, a material with high dispersion, that is low Abbe number, is selected for the negative lens 21. The positive lens 22 has a material with low dispersion, that is high Abbe number. Here, the difference in the two Abbe numbers preferably lies between 16 and 22. Both the negative lens 21 and the positive lens 22 are preferably manufactured from a material having a high refractive index, preferably with a refractive index greater than or equal to 1.6. By using lenses with high refractive index, it is possible simultaneously to correct necessary corrections of the monochromatic image aberrations, such as spherical aberration, coma or astigmatism. The monochromatic image aberrations can be corrected further if the positive lens 22 and the negative lens 21 have approximately identical focal lengths, but with different signs.

A very good high-contrast image quality is achieved if the color ranges of the right-hand component beams (31, 32, 33) of the right-hand observation beam path 30 and the color ranges of the left-hand component beams (41, 42, 43) of the left-hand observation beam path are in each case perceived to be congruent in the eyepiece intermediate image plane (34, 35). To this end, it is necessary for a chromatic angle deviation which is less than 0.5' to be achieved for all wavelength ranges of the visible light between 480 nm and 660 nm.

As shown in FIG. 2, the object-side and the image-side focal lengths of the optical system in respect of the two main planes H and H' are in each case dependent on the wavelength λ. Here, the following three focal lengths are important:

$f_e$=object-side focal length for the main wavelength e in respect of the first main plane H;

$f_\lambda$=object-side focal length for the wavelength λ in respect of the first main plane H;

$f_e'$=image-side focal length for the main wavelength e in respect of the second main plane H'.

If the lens system is embodied in such a way, that is if the reduction optical unit, which includes the negative lens 21 and the positive lens 22, and the main objective 20 are matched to one another in such a way, that the following relation is satisfied for a wavelength range λ of 480 nm≤λ≤660 nm and for a main wavelength e=546 nm:

$$\left|\arctan\left(\frac{B}{f_e' + (f_e \cdot f_e'/(f_\lambda - f_e))}\right)\right| < 0.5',$$

then the imaging quality for an observation beam path is corrected so well that an unchanging good contrast of the imaging and an unchanging, very good image quality over the whole wavelength range λ are achieved. As a result of this, the color ranges of the right-hand component beams (31, 32, 33) of the right-hand observation beam path 30 and the color ranges of the left-hand component beams (41, 42, 43) of the left-hand observation beam path are respectively perceived as being congruent in the eyepiece intermediate image plane (35, 45). As a result, a chromatic angle deviation which is less than 0.5' is achieved.

By way of example, for a wavelength λ=660 nm, the chromatic angle deviation CWA can be calculated as follows for the exemplary embodiment:
fe=−175.102 mm (for e=546 nm)
fe'=+175.102 mm (for e=546 nm)
fλ=−175.033 mm (for λ=660 nm)
B=12 mm.
Therefore, the following emerges for the CWA (in minutes of arc):

$$CWA = \left|\arctan\left(\frac{B}{fe' + (fe \cdot fe'/(f\lambda - fe))}\right)\right|$$

$$= \left|\arctan\left(\frac{12 \text{ mm}}{175.102 \text{ mm} + \left(\frac{-175.102 \text{ mm} \cdot 175.102 \text{ mm}}{(-175.033 \text{ mm} - (-175.102 \text{ mm}))}\right)}\right)\right|$$

$$= 0.093'$$

Since 0.093'<0.5', the condition for good image quality with a low chromatic angle deviation CWA is satisfied for a wavelength λ=660 nm and a main wavelength e=546 nm.

If this condition is satisfied for all wavelengths λ between 480 nm and 660 nm, the selected material and form combination for the negative lens 21 and the positive lens 22 of the reduction optical unit is suitable for satisfying the object.

It is desirable for there to be no need for changing the focus setting of the microscope when the reduction optical unit is introduced into the observation beam paths (30, 40). To this end, it is advantageous if the reduction optical unit can change the focal length, that is focus onto the image plane 10. In the exemplary embodiment in FIG. 1, the overall focal length $F_{ges}$ of the optical system, which includes the main objective 20 and the reduction optical unit, is selected in such a way that it lies in the range between 0.7-times and 1.1-times the focal length of the main objective $F_{HO}$. This value is sufficient to enable focusing on the image plane 10 by the reduction optical unit. To this end, the negative lens 21 is disposed in a stationary manner and the positive lens 22 is disposed in a displaceable manner along the optical axis 23 as indicated by the double-headed arrow 24 above the positive lens 22 in FIG. 1. In an alternative embodiment, it is also possible for the positive lens 22 to be disposed in a stationary manner and for the negative lens 21 to be disposed in a displaceable manner along the optical axis 23. FIG. 1 shows a central focus setting with a focal length $F_{ges}$=0.87*$F_{HO}$.

The diagram in FIG. 3 shows a result for suitable material and form stipulation for the negative lens 21 and the positive lens 22 which, for the wavelengths of the visible light and various focus settings, supplies a chromatically corrected, high-contrast image.

FIG. 3 depicts an image-side chromatic angle deviation CWA in relation to a wavelength λ in the visible range between 480 nm and 660 nm for three different focal lengths of the first exemplary embodiment.

The diagram 200 shows the chromatic angle deviation CWA in minutes of arc on the Y-axis in a range from −0.5' to +0.5'. The X-axis plots the wavelength range λ between 480 nm and 660 nm. The main wavelength e=546 nm is highlighted by a dashed line 204. The chromatic angle deviation CWA is depicted for three focal lengths: a first focal length $F_{ges}$=0.80*$F_{HO}$ is depicted by a first curve 201; a second focal length $F_{ges}$=0.87*$F_{HO}$ is depicted by a second curve 202 and a third focal length $F_{ges}$=0.96*$F_{HO}$ is depicted by a third curve 203. The first curve 201 and the third curve 203 in each case show the focus setting in a possible final position.

For the central focus setting with a focal length $F_{ges}$=0.87*$F_{HO}$, the image-side chromatic angle deviation CWA is corrected particularly well for the whole wavelength range λ between 480 nm and 660 nm, and lies in the range between −0.1' and zero, see the second curve 202. For the main wavelength e=546 nm, the chromatic angle deviation CWA equals zero.

The chromatic angle deviation CWA for a focus setting with the focal length $F_{ges}$=0.80*$F_{HO}$ lies in the range between +0.28' and −0.45' for the whole wavelength range λ between 480 nm and 660 nm, see the first curve 201. The chromatic angle deviation CWA also equals zero for the main wavelength e=546 nm in this focus setting.

The image-side chromatic angle deviation CWA for a focus setting with the focal length $F_{ges}$=0.97*$F_{HO}$ lies in the range between −0.39' and +0.24' for the whole wavelength range λ between 480 nm and 660 nm, see the third curve 203. The image-side chromatic angle deviation CWA also equals zero for the main wavelength e=546 nm in this focus setting.

The curves 201, 202 and 203 clearly show that the image-side chromatic angle deviation CWA lies in the range of +/−0.5' for all focal lengths over the whole focusing range.

Hence, an optical imaging system 1 is provided which, when using a reduction optical unit, which can be introduced into a beam path (30, 40), which can be focused and which includes a negative lens 21 and a positive lens 22, achieves a very short structural length ahead of a main objective. This optical imaging system achieves a very good image quality over the whole focusing range while having a very low chromatic angle deviation.

The reduction optical unit (21, 22) can be pivoted into the beam path ahead of the main objective 20. In order to enable the user of a microscope to work alternatively with or without the reduction optical unit, it is advantageous if the reduction optical unit (21, 22) can be simply introduced into the beam path or removed from the beam path as indicated by the double arrow 25. As a result, the user can quickly and easily switch back-and-forth between two focus planes without having to change the focus setting of the microscope.

It is understood that the foregoing description is that of the preferred embodiments of the invention and that various changes and modifications may be made thereto without departing from the spirit and scope of the invention as defined in the appended claims.

LIST OF REFERENCE SIGNS

1 Optical imaging system
2 Eye
3 Ophthalmic lens
10 Image plane
20 Main objective
21 Negative lens
22 Positive lens
23 Optical axis
24 Double arrow indicating displaceability along optical axis of lens 22
25 Double arrow indicating movability of optical reduction unit (21, 22) into and out of beam path
30 Right-hand observation beam path
21 Right-hand red component beam
32 Right-hand green component beam
33 Right-hand blue component beam
34 Right-hand tube lens
35 Right-hand eyepiece intermediate image plane
36 Right-hand eyepiece
40 Left-hand observation beam path
41 Left-hand red component beam
42 Left-hand green component beam
43 Left-hand blue component beam
44 Left-hand tube lens
45 Left-hand eyepiece intermediate image plane
46 Left-hand eyepiece
101 First ray of the beam path from the object point O to the main plane H in the object space
102 Second ray of the beam path between the main planes H and H'
103 Third ray of the beam path from the main plane H' to the image point O' in the image space
200 Diagram of chromatic angle deviation CWA
201 First curve, CWA for $F_{ges}=0.80F_{HO}$
202 Second curve, CWA for $F_{ges}=0.87F_{HO}$
203 Third curve, CWA for $F_{ges}=0.96F_{HO}$
204 Dashed line, main wavelength e=546 nm

What is claimed is:

1. An optical imaging system for generating an image of an object plane, the optical imaging system defining an optical axis and comprising:
   a lens system including a main objective and a reduction optical unit arranged between said main objective and said object plane;
   said lens system being aligned along said optical axis;
   said reduction optical unit including a first lens having a positive refractive power and a second lens having a negative refractive power;
   said lens system defining an object-side first main plane (H) and an image-side second main plane (H');
   said optical imaging system defining an observation beam path which is guided through said lens system so as to cause said observation beam path to be at a distance B from the optical axis of the lens system in each of said first main plane (H) and said second main plane (H');
   said first lens being made from a first material having a first Abbe number;
   said second lens being made from a second material having a second Abbe number;
   said first Abbe number being greater than said second Abbe number; and,
   said lens system being configured so as to cause the following relation to be satisfied for a wavelength range λ of 480 nm≤λ≤660 nm and for a main wavelength e=546 nm:

$$\left|\arctan\left(\frac{B}{f'_e + (f_e \cdot f'_e/(f_\lambda - f_e))}\right)\right| < 0.5'$$

wherein:
   $f_e$ =object-side focal length for the main wavelength (e) with respect to said first main plane (H);
   $f_\lambda$ =object-side focal length for the wavelength λ with respect to said first main plane (H); and,
   $f_e'$ =image-side focal length for the main wavelength (e) with respect to said second main plane (H').

2. The optical imaging system of claim 1, wherein said first material and said second material are selected so as to cause a difference between said first Abbe number and said second Abbe number to lie between 16 and 22.

3. The optical imaging system of claim 1, wherein:
   said first material has a first refractive index;
   said second material has a second refractive index;
   said first material and said second material are selected so as to cause said first refractive index to be greater than 1.6 and said second refractive index to be greater than 1.6.

4. The optical imaging system of claim 1, wherein said first lens is fixedly mounted and said second lens is mounted so as to be displaceable in the direction of said optical axis.

5. The optical imaging system of claim 1, wherein said second lens is fixedly mounted and said first lens is mounted so as to be displaceable in the direction of the optical axis.

6. The optical imaging system of claim 1, wherein said reduction optical unit is configured to be pivotable into the beam path on the image side of said main objective.

7. The optical imaging system of claim 1 further comprising:
   an additional optical element configured to generate an intermediate image;

said additional optical element being mounted in said observation beam path on the image side of said reduction optical unit; and, said optical imaging system being focused onto said intermediate image.

8. The optical imaging system of claim 1, wherein:

the optical imaging system is configured as a stereo microscope;

said observation beam path includes a first observation beam path and a second observation beam path; and, said first and said second observation beam paths, in said first main plane (H) and in said second main plane (H'), each are at a distance (B) from said optical axis of said lens system.

* * * * *